United States Patent [19]

Deguemp

[11] 4,203,216
[45] May 20, 1980

[54] MAGNETIC PROSTHETIC ELEMENT

[76] Inventor: Jean-Antoine E. Deguemp, 20 rue de Vintimille, 75009 Paris, France

[21] Appl. No.: 911,871

[22] Filed: Jun. 2, 1978

[30] Foreign Application Priority Data

Jun. 2, 1977 [FR] France .................................. 77 16822

[51] Int. Cl.² ........................ A61C 13/00; A61C 13/22
[52] U.S. Cl. ............................................................ 32/2
[58] Field of Search ................ 32/2, 8, 10 A, DIG. 6, 32/5, 6, 7

[56] References Cited

U.S. PATENT DOCUMENTS 3,514,859 6/1970 Peterson .................................... 32/2
3,646,676 3/1972 Mitchell .................................... 32/2

Primary Examiner—Russell R. Kinsey
Assistant Examiner—Michael J. Foycik, Jr.
Attorney, Agent, or Firm—Finnegan, Henderson, Farabow, Garrett & Dunner

[57] ABSTRACT

A magnetic device for retaining a dental prosthesis on a jawbone. Magnetic material is solidly fastened in a support adjustably movable in a frame rigidly fixed to the prosthesis for interacting with magnetic material seated in a cavity in the jawbone. A threaded eccentric gear and a rack cooperate with pinions accessible from outside the frame, for respectively adjusting the relative positions of the magnetic materials axially and laterally.

7 Claims, 7 Drawing Figures

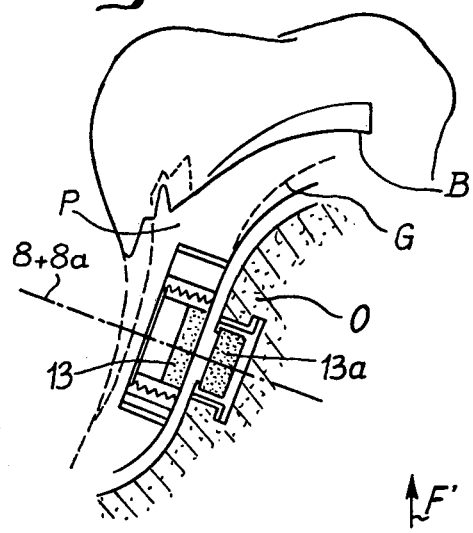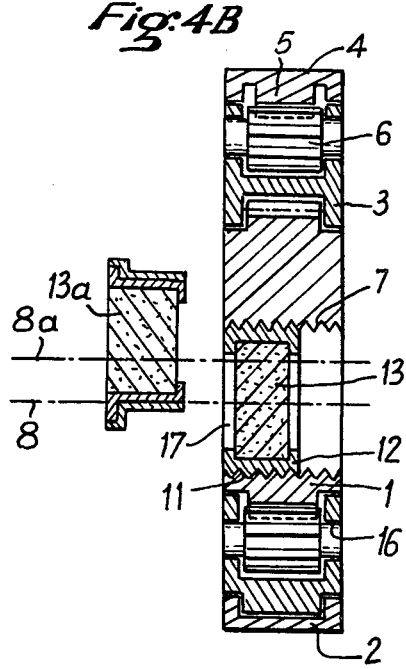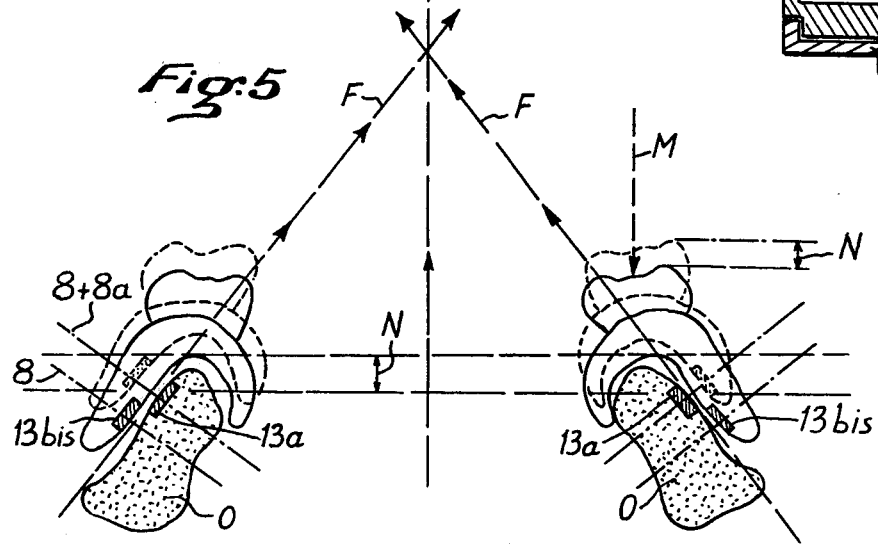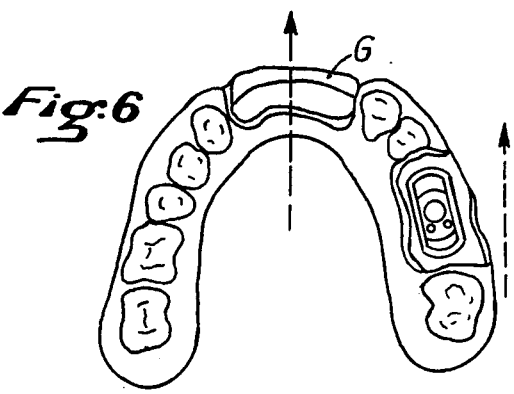

ately, the magnetic
MAGNETIC PROSTHETIC ELEMENT

BACKGROUND OF THE INVENTION

The invention relates to a device for retaining a prosthesis element on an osseous segment or part, in particular to a dental prosthesis, which can be fitted in removable manner on the jawbone.

The conventional mechanical devices for retaining a prosthesis element on an osseous segment, using such as cuppings, springs or special geometries, besides occasionally causing painful pressures on the mucous membrane, are not very effective and are poorly tolerated.

The fixation of prosthetic retaining implants in bone foundation of the jawbone has already been proposed. Such a technique, however, entails passing through the mucous membrane and maintaining the fixing components in position which may cause microbial infections and the irreversible destruction of the osseous foundation.

A recent solution offering many advantages consists in retaining the prosthetic element by magnetic forces generated by one or several magnetic systems each including a magnetic or magnetizable material implanted internally in a cavity made in the bone foundation and of a magnetic or magnetizable material contained externally in the prosthetic element. Hereafter, a magnetic material, whether used internally or externally, will denote a magnetic as well as a magnetizable element in each magnetic system, at least one of the elements being a true magnet.

The object of the present invention consists in improvements in the magnetic material contained externally in the prosthetic element as regards its structure, its assembly and its retaining means.

The co-pending U.S. Patent application Ser. No. 772,999, filed Feb. 28, 1977 in the name of the same inventor discloses how to associate a base structure, to be located in the clearance cavity made in the osseous segment, with the internal magnetic material, means furthermore being provided to lock the base structure in the clearance cavity once it has been inserted into it, and also means being provided to retain, preferably in removable manner, the magnetic material on the base structure.

In this fashion, the position of the internal magnetic material is entirely determined.

It is, however, required that the magnitude of the magnetic force generated by the interaction of the two magnetic materials correspond perfectly to the requirement at hand, i.e., achieving sufficient but not excessive retention, so as to avoid unbearable compression of the mucous membrane.

As already stated, the retention of the internal magnetic material on its base structure preferably is implemented in a removable manner, and in theory, at least, one may try successively several magnetic elements of different strengths in order to obtain the precisely fitting magnetic force required. However, each new effort would require another manipulation and this would rapidly become intolerable to the patient. The ability to remove the internal material is justified only in view of a possible ultimate loss of magnetic power of said material which then would have to be replaced.

Accordingly, elements preferably are so selected that the retention of the prosthesis is reliably obtained, and preferably means are provided to adjust the magnitude of the air gap, or other gap between the magnetic pole faces, to keep the compression on the mucous membrane within reasonable limits. Furthermore, the magnetic field seeks its own maximum, that is, the magnetic forces tend to so displace the two conjugate magnetic materials that their axes will tend to coincide, and therefore, the position of the external magnetic material can be adjusted to be in a plane parallel to that of the front face of the internal material, whereby the prosthesis will rest on the jawbone only very lightly outside the periods of use (for instance when chewing). Not only does the magnetic field provide for the retention of the prosthesis, but furthermore, it acts as a permanent and stable shock absorber.

One object of the invention is to ensure that the external magnetic material is rigidly mounted to a support, itself fixed in a frame fastened to the prosthesis and housed in the latter's thickness, means being provided to adjust—preferably in continuous manner—the relative position of the support in the frame, on one hand in a plane parallel to that of the front face of the internal material so as to adjust the relative position of the axes of the internal and external magnetic materials, and on the other hand, in a direction perpendicular to this plane so as to adjust the gap between the magnetic poles.

BRIEF DESCRIPTION OF THE DRAWING

An embodiment will now be described in non-limiting manner below, in relation to the attached drawings.

FIG. 4A is a section through the device, the internal and external magnetic materials being shown in interacting positions;

FIG. 4B is a section similar to FIG. 4A, but from a different angle;

FIG. 5 shows the effect of bilaterally controlling the device as regards the prosthesis position; and FIG. 6 is a top view, partially cut away, of a prosthesis in position on the lower maxilliary, illustrating the device on one hand and the sagittal displacement of the prosthesis with respect to the crest on the other, which displacement is particularly sizable in the incisor region when the mechanism causing the case to move within the frame in that direction is actuated.

DESCRIPTION OF THE PREFERRED EMBODIMENT

Figure 1:
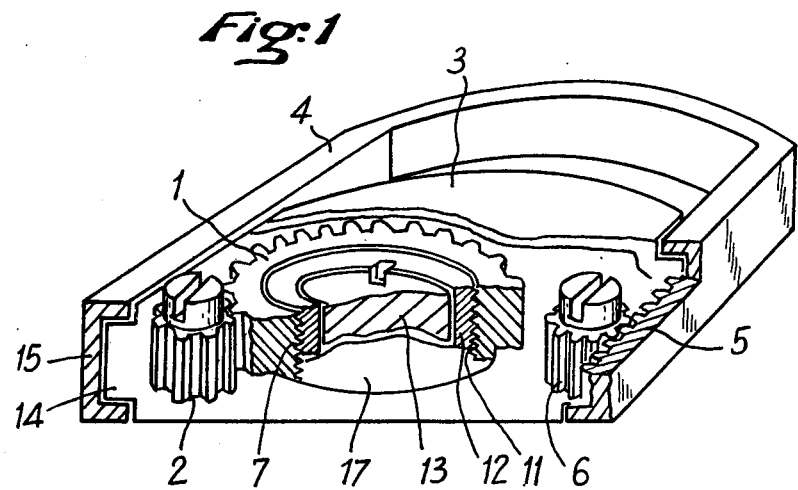
FIG. 1 is a perspective, partially cut away, of an embodiment of the external material support of the invention.

The magnetic device for retaining a prosthesis element P on the gum fibromucous membrane G of a lower maxillary O (FIGS. 4A, 4B, 5 and 6) comprises an external magnetic material 13 housed in the prosthetic element and an internal magnetic material 13a seated in a clearance cavity made in the osseous foundation.

In conformity with the corresponding patent application Ser. No. 772,999 cited above, the method and method for implanting the internal magnetic material will be described for facilitating the understanding of the invention. The internal material 13a is associated with a support structure and the clearance at its bottom has a cross-section larger than the entrance cross-section at the outer surface of the osseous segment, locking means for the support structure consisting of projections extending outward and for the purpose of coming to rest against the bone inside the lower extensions of the clearance, at least one of said projections being eliminated when the device is inserted into the clearance.

Advantageously, the clearance consists of a cylindrical cavity flaring at its base, while the support structure consists of a flexible blade, for instance made of stainless steel and very thin (less than 1/10 of a mm) which coils on itself to form a cut ring with overlapping edges. It is understood that such a ring is very elastic and that a side pressure exerted on it contributes to decreasing its diameter at rest.

The lower rim of the ring comprises a number of lugs separated from one another by slits, the ends of said lugs being bent nearly perpendicularly to the side of the ring towards the outside so as to form a collar of circumferential clamps.

The upper rim of the ring comprises little tongues that can be bent inward so as to keep magnet 13a inside the ring.

Insertion is carried out by placing only the ring (without the magnet) into the clearance cavity in the bone. The diameter of the clamp collar, when in the rest state, is larger than the diameter at the entrance to the cavity, and, therefore, the ring diameter is reduced by compressing it from the sides so as to allow it to enter the cavity.

Once in place, the ring expands and the clamps wedge themselves inside the cavity. Thereupon, it is only necessary to place the magnet 13a into the ring, to bend the upper tongues against the magnet, for the whole to be locked in position in the bone without there being the possibility of accidental removal.

A simple control allows easy manipulation and emplacement of the ring described above under conditions of strict asepticism.

This control consists of a hollow, cylindrical body open at its base and provided with a gripping means such as a knob at its upper part. Two oblong and diametrically opposite slots parallel to the axis and beginning at the base are provided in the lateral wall of this cylindrical body.

A removable disc with a diameter slightly less than the inside diameter of the hollow body penetrates inside of it, this disk including two diametrically opposite rods penetrating through the slots of the hollow body. Finally, the ring is inserted into this body, underneath the disk, under diametrical stress, the circumferential clamps pressing against the lower edge of the hollow body.

The ring for holding the internal magnetic material is emplaced in the clearance in the following manner:

The set of hollow body and ring is kept in sterile packing (flask) until use. It is enough to take hold of the gripping knob with pinchers to remove the set from its packing and then to insert it into the clearance. When the set is in a proper position at the bottom of the cavity, a pressure is exerted with a suitable instrument on the rods of the removable disk, and simultaneously the hollow body is withdrawn by pulling on the knob. The disk therefore keeps the ring inside the cavity while the hollow body is being removed from it. The released ring expands and assumes its permanent position in the bottom of the cavity. Afterward, the disk is simply removed and magnet 13a is emplaced in the ring.

It will be noted that the hollow body and the disk may advantageously be made of plastic.

An implementation of the assembly of the external magnetic material according to the invention will now be described in relation to FIGS. 1 through 6.

Even though they represent the same implementation, the Figures are at different scales for the sake of greater clarity with respect to the constituent parts or details shown.

It is understood, of course, that the materials used for the various components other than those which are specified as magnetic or magnetizable are non-magnetic.

The drawings show the external magnetic or magnetizable material 13 solidly fastened to a ring 12 by any suitable means, such as bonding, clamping, crimping, etc.

Ring 12 includes an outside thread 11.

Material 13, together with its ring 12, is displaceably mounted by the intermediary of its support—which is a gear 1—inside a case 3, of which the upper face includes adjustment holes 16, to be discussed further below.

Both the upper and the lower faces of case 3 include circular windows 17 in which pivots the support gear 1 with its toothed crown.

The support 1 engages by its toothed crown a pinion 2 supported on the bottom of the case 3 and including a slotted end accessible through adjustment hole 16.

An eccentric and threaded bore 7 into which is screwed the threaded ring 12, which latter is of a height less than the thickness of support 1, passes through the support so that when the support pivots in case 3, ring 12 will move like a cam, which shall be its designation hereafter. Furthermore, the screwing or unscrewing of cam 12 in its support 1, which is thicker, allows varying the distance between the front face of material 13 from the plane of the lower face of case 3.

Case 3 is mounted to slide within a frame 4 by means of side guides 14 operating in glide surfaces 15 forming the longitudinal sides of said frame 4.

Frame 4 is to be mounted in prosthesis P and held within its thickness, as shown by FIGS. 4A through 6, furthermore being so fastened that the control mechanisms can be reached through the upper window which is kept clear during the course of making the prosthesis, and thereafter, hermetically sealed when the adjustments have been made.

FIG. 1 shows the external magnet 13 held within the cam in the form of ring 12, with the threads 11 engaging the corresponding threads of the eccentric bore 7 of support 1.

Support 1, by its toothed crown, meshes with a pinion 2, both of these components being located inside case 3, of which the upper and lower rims penetrate the grooves of frame 4, which itself is joined to the prosthesis P by suitable retaining means.

One of these grooves holds within its cavity a gear rack 5 meshing with a pinion 6 that is rotatably mounted in case 3.

Figure 2:
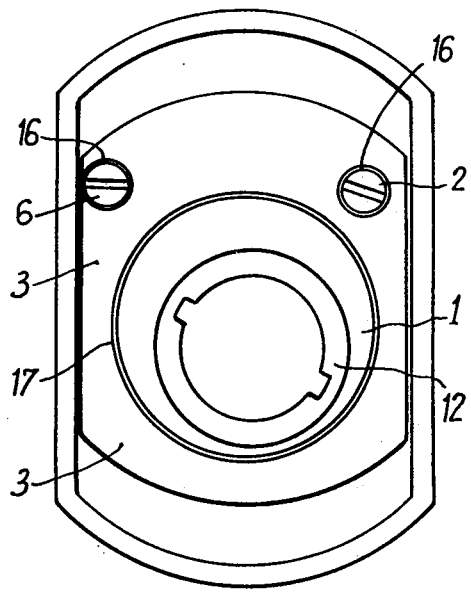
FIG. 2 is a top view of the support of FIG. 1.

FIG. 2 is a top view of the device, wherein case 3 holds the assembly of support 1 and pinions 2 and 6, the hollowing of its upper face being opposite support 1 of which only the toothed crown is within the case, so that the rotational surface of cam 12 be entirely clear and so that no part of the case interferes and prevents accessibility to the control screw for the gap between the poles.

The lower face, which is omitted, comprises a similar hollow so that the magnetic field will not be interrupted.

Figure 3:
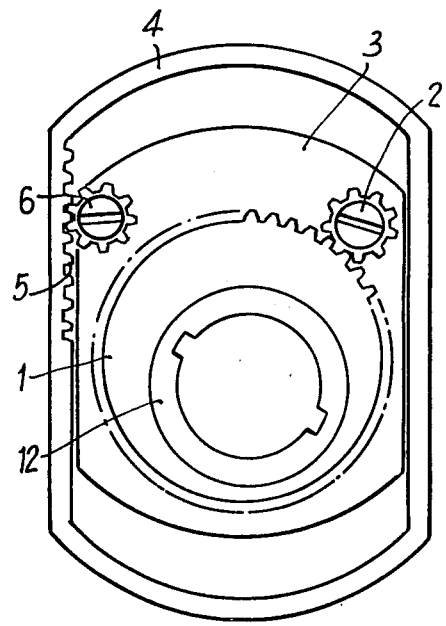
FIG. 3 is a view similar to FIG. 2, the upper face of the case having been removed.

FIG. 3 shows the device at the same angle as FIG. 2, but following removal of the case cover and of the corresponding side of the groove of frame 4. This figure shows pinion 2 meshing with the toothed crown of support 1, and it is evident that by using a screwdriver on the slotted end of pinion 2, rotation may be imparted to the pinion, which in turn, makes the support gear rotate in the opposite direction, whereby cam 12 can be displaced.

It is furthermore seen that a similar actuation of pinion 6 makes the case move rectilinearly with respect to the gear rack 5.

FIG. 4A shows a frontal section of the lower maxillary O at the level of the molar region, the prosthesis P resting by the curvature of its base B on the gum fibromucous membrane G, the magnetic system comprising the internal magnet 13a in bone O and the external magnet 13 integrated into prosthesis P being in their normal operating position to ensure the ideal retention of this prosthesis.

FIG. 4B shows the device in sagittal section after actuation of the cam has caused a change in the relative positions of materials 13 and 13a of which the previously coinciding axes 8 and 8a now have been translated by a distance Q.

FIG. 5 is a frontal section of the two branches of jawbone O.

Starting with the position shown in FIG. 4A, it is seen that the prosthesis P, which is rigidly fixed to the device, has undergone a displacement N due in particular to the chewing pressure M, whereby the external magnetic material 13 has been moved to position 13 bis where M is a maximum.

In such a position, where the axes 8 and 8a of materials 13 and 13a, respectively, are apart a distance N, the magnetic force F tends to cancel said displacement by acting on either of the prosthesis branches and becomes a resultant force F' which secures to the largest extent possible the materials 13 and 13a to each other, this being obtained when the respective axes 8 and 8a coincide again, whereupon the prosthesis is in its rest position.

In view of its design, the device is fastened on the prosthesis with its upper face toward the prosthesis' vestibular side, where it is easily accessible, so that the different adjustments provided for can be made for the purpose of satisfactory retention compatible with the least adhesion to the jawbone.

Preferably, the patient should be given a few days to get used to the prosthesis and any corrections required should be made thereafter.

The prosthesis then will be completed by protecting the mechanisms by suitable means, since the final adjustment basically is definitive. However, it is also prudent to provide for any ulterior hazards: loss in magnetic intensity in the materials, changes in the bone crest requiring a new foundation, for instance.

Embodiments different from those described are possible, in particular, when space is insufficient. In such cases, use must be made of devices allowing at least two predetermined positions, without there being the possibility of continuous adjustment. Such a simplified apparatus comprises a pushrod or lever control of the external material moving between these two modes of operation and rest.

The same difficulty also requires replacing the magnetic material represented by the magnet—there being limits to the degree of its miniaturization—with a magnetizing material of small volume, at the cost of a more powerful internal magnet.

Many variations are possible, some applying to special cases, in particular where several internal magnets are required in the absence of a suitable osseous foundation. In such a case, the prosthesis must comprise a magnetic material with a surface at least equal to the periphery enclosing the internal magnets and capable of at least one-dimensional control.

What is claimed is:

1. A magnetic device for retaining a prosthetic element, in particular, a dental prosthesis, on a bone segment, in particular the jawbone, the device comprising an internal magnetic or magnetizable material, preferably seated in removable manner in a cavity fashioned in said bone, said internal magnetic or magnetizable material interacting with an external magnetic or magnetizable material seated in the prosthesis, a frame rigidly fixed to the prosthesis, a support mounted in said frame and housed within its thickness, said external material being solidly fastened to said support; and means to control, preferably in continuous manner, the relative position of said support in said frame, on one hand in a plane parallel to that of the front face of said material so as to adjust the relative position of the axes of the internal and external materials, and on the other hand in a direction perpendicular to this plane so as to adjust the magnitude of the gap between pole pieces.

2. A magnetic device according to claim 1 also including a case for holding said support and conjugate drive means mounted both on the support and the case for displacing said support parallel to the bottom of the case, and wherein said case is slidably mounted in an adjustable manner in the frame in the sagittal direction of the prosthesis, while the support is positionally adjustable in the direction perpendicular to the case bottom by its drive means, said case including access holes for facilitating adjusting the positions of said case and support.

3. A magnetic device according to claim 2, characterized in that the support consists of a gear having an eccentric thread bored therethrough, said device also including a threaded eccentric ring seating in said eccentric thread for holding the external material, the means driving the support being the toothed crown of the gear kept fixed but free to rotate within the case using conjugate undercuts and shoulders, said support also being thicker than the eccentric ring which thereby may be screwed into or out of the threaded bore, and in that the drive means mounted on the case consist of a pinion meshing with the gear and having a slotted end accessible from outside the case through a corresponding access hole.

4. A magnetic device according to either of claims 1 or 2, also including a pinion for controlling the sliding of the case in the frame, said pinion having a slotted end accessible from outside the case by a corresponding access hole for actuating the pinion and a gear rack mounted to one of the longitudinal sides of the frame for meshing with the pinion.

5. A magnetic device according to either of claims 1 or 2, characterized in that the support for the external material is mounted in sliding manner within the thickness of the prosthesis and wherein said device includes a pushrod outside the prosthesis for actuating the support towards at least two end positions with stopping means.

6. A magnetic device according to claim 5, also including a level outside the prosthesis for actuating the sliding support, the support being lockable in at least two end positions by suitable stop means.

7. A magnetic device according to either of claims 1 or 2, also including means outside the prosthesis for moving the support holding the external material within the thickness of the prosthesis in curvilinear manner and wherein said support can be held in at least two end positions by suitable stopping means.

* * * * *